(12) United States Patent
Yavorsky et al.

(10) Patent No.: US 10,821,225 B2
(45) Date of Patent: Nov. 3, 2020

(54) CANNULAS FOR DRUG DELIVERY DEVICES

(71) Applicant: Medtronic MiniMed, Inc., Northridge, CA (US)

(72) Inventors: Matthew William Yavorsky, Granada Hills, CA (US); Pablo Vazquez, Porter Ranch, CA (US)

(73) Assignee: MEDTRONIC MINIMED, INC., Northridge ( * ) Notice: Subject to any disclaimer, the term of this patent is extended or adjusted under 35 U.S.C. 154(b) by 126 days.

(21) Appl. No.: 15/850,302

(22) Filed: Dec. 21, 2017

(65) Prior Publication Data

US 2018/0207355 A1 Jul. 26, 2018

Related U.S. Application Data

(60) Provisional application No. 62/448,777, filed on Jan. 20, 2017, provisional application No. 62/448,785, (Continued)

(51) Int. Cl.

| A61M 5/158 | (2006.01) |
|---|---|
| A61M 39/08 | (2006.01) |
| A61L 31/04 | (2006.01) |
| A61L 31/06 | (2006.01) |
| A61L 29/14 | (2006.01) |
| A61L 29/06 | (2006.01) |
| A61L 29/04 | (2006.01) |
| A61M 5/32 | (2006.01) |

(52) U.S. Cl.
CPC ........... *A61M 5/158* (2013.01); *A61L 29/041* (2013.01); *A61L 29/06* (2013.01); *A61L 29/14* (2013.01); *A61L 31/048* (2013.01); *A61L 31/06* (2013.01); *A61M 39/08* (2013.01); *A61M 2005/3201* (2013.01); *A61M 2205/0216* (2013.01)

(58) Field of Classification Search
CPC .. A61M 2005/3201; A61M 2205/0216; A61M 39/08; A61M 5/158; A61L 29/041; A61L 29/06; A61L 29/14; A61L 31/048; A61L 31/06; C08L 27/12; C08L 75/04
See application file for complete search history.

(56) References Cited

U.S. PATENT DOCUMENTS

| 4,335,718 A | 6/1982 | Calabrese |
| 4,755,173 A | 7/1988 | Konopka et al. |

(Continued)

FOREIGN PATENT DOCUMENTS

| EP | 1459691 A1 | 9/2004 |
| WO | 2013103864 A1 | 7/2013 |

OTHER PUBLICATIONS

PCT Search Report and Written Opinion for PCT/US2017/068269 dated May 25, 2018.

*Primary Examiner* — Brandy S Lee
(74) *Attorney, Agent, or Firm* — Lorenz & Kopf, LLP (57) ABSTRACT

Embodiments relate to a cannula that is provided for delivering a substance, such as a medicine (e.g., insulin) to a patient, where the cannula has reduced likelihood of kinking or occlusions when implanted in a patient. The cannula may have a reduced number of stress concentrations along its length, an angled tip and/or a curve in its length. The cannula may include other designs to reduce kinking, such as internal ribbing and/or a slit along its wall.

13 Claims, 9 Drawing Sheets

Related U.S. Application Data filed on Jan. 20, 2017, provisional application No. 62/448,794, filed on Jan. 20, 2017, provisional application No. 62/448,798, filed on Jan. 20, 2017.

(56) References Cited

U.S. PATENT DOCUMENTS

| | | | |
|---|---|---|---|
| 5,391,250 A | 2/1995 | Cheney, II et al. | |
| 5,485,408 A | 1/1996 | Blomquist | |
| 5,522,803 A | 6/1996 | Teissen-Simony | |
| 5,665,065 A | 9/1997 | Colman et al. | |
| 5,800,420 A * | 9/1998 | Gross | A61K 9/0021 604/890.1 |
| 5,807,375 A | 9/1998 | Gross et al. | |
| 5,925,021 A | 7/1999 | Castellano et al. | |
| 5,954,643 A | 9/1999 | Van Antwerp et al. | |
| 6,017,328 A | 1/2000 | Fischell et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,544,212 B2 | 4/2003 | Galley et al. | |
| 6,558,351 B1 | 5/2003 | Steil et al. | |
| 6,591,876 B2 | 7/2003 | Safabash | |
| 6,641,533 B2 | 11/2003 | Causey, III et al. | |
| 6,736,797 B1 | 5/2004 | Larsen et al. | |
| 6,749,587 B2 | 6/2004 | Flaherty | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,399,277 B2 | 7/2008 | Saidara et al. | |
| 7,442,186 B2 | 10/2008 | Blomquist | |
| 7,602,310 B2 | 10/2009 | Mann et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Hunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 2007/0123819 A1 | 5/2007 | Mernoe et al. | |
| 2010/0160861 A1 | 6/2010 | Causey, III et al. | |
| 2013/0317476 A1* | 11/2013 | Searle | A61M 25/0045 604/506 |
| 2015/0051583 A1* | 2/2015 | Horvath | A61M 25/0015 604/508 |

* cited by examiner

CANNULAS FOR DRUG DELIVERY DEVICES

CROSS-REFERENCE TO RELATED APPLICATION

The present disclosure claims the benefit of and priority to U.S. Provisional Patent Applications 62/448,777; 62/448,785; 62/448,794; and 62/448,798 each filed on Jan. 20, 2017, the contents of which are hereby incorporated by reference in their entirety.

BACKGROUND OF THE DISCLOSURE

Field of the Disclosure

The present disclosure generally relates to cannula designs for drug delivery devices, such as insulin pumps. More particularly, the present disclosure relates to improved designs of cannulas that prevent kinking during insertion in the body of a user, for example cannulas that include bent tubing.

Description of the Related Art

Insulin must be provided to people with Type 1 and many with Type 2 diabetes. Traditionally, since it cannot be taken orally, insulin has been injected with a syringe. More recently, use of external infusion pump therapy has been increasing, especially for delivering insulin for diabetics using devices worn on a belt, in a pocket, or the like, with the insulin delivered via a catheter with a percutaneous needle or cannula placed in the subcutaneous tissue. For example, as of 1995, less than 5% of Type 1 diabetics in the United States were using pump therapy. There are now about 12% of the currently over 1,000,000 Type 1 diabetics in the U.S. using insulin pump therapy, and the percentage is now growing at an absolute rate of over 2% each year. Moreover, the number of Type 1 diabetics is growing at 3% or more per year. In addition, growing numbers of insulin using Type 2 diabetics are also using external insulin infusion pumps. Physicians have recognized that continuous infusion provides greater control of a diabetic's condition, and are also increasingly prescribing it for patients. In addition, medication pump therapy is becoming more important for the treatment and control of other medical conditions, such as pulmonary hypertension, HIV and cancer.

Subcutaneous infusion sets are generally known in the medical arts for use in the administration of a selected medication or other therapeutic fluid to a desired subcutaneous infusion site located beneath the skin of a patient. Such infusion sets typically include a tubular cannula or catheter that is supported by and protrudes from a compact housing adapted to receive the infusion fluid via delivery or infusion tubing, which is suitably connected to other components of the fluid infusion system. Infusion sets can be used, for example, to transport insulin from an insulin pump to a subcutaneous site in a patient. The subcutaneous infusion set normally includes an insertion needle, which is assembled with the soft cannula and is adapted to pierce the patient's skin for transcutaneous cannula placement. The insertion needle is thereafter withdrawn to leave the cannula in place for subcutaneous fluid infusion. Exemplary subcutaneous infusion sets of this general type are described in U.S. Pat. Nos. 4,755,173; 5,176,662; and 5,257,980, which are incorporated by reference herein. Such subcutaneous infusion sets are commonly used with compact medication infusion pumps for programmable administration of medication such as insulin. Exemplary infusion pumps of this general type are described in U.S. Pat. Nos. 4,562,751; 4,678,408; and 4,685,903, which are incorporated by reference herein.

Although the material used for such cannulas are flexible enough to provide comfort for the patient, kinking of the cannulas can also result. If a cannula becomes kinked, the opening in the cannula may become occluded in whole or in part, resulting in a limited or complete lack of supply of medication being provided to a patient.

SUMMARY OF THE DISCLOSURE

In aspects, provided herein are cannulas for infusion of medication, wherein the cannulas provide reduced chances of kinking or occlusions when the cannulas are implanted in patients. In particular aspects, a cannula is provided, the cannula comprising a tube adapted to be inserted into the skin of a patient, the tube having a wall with an internal surface and an external surface and having a first portion connected to a drug delivery device and a second portion, wherein the lower portion of the tube includes a tip at the end of the tube opposite to the attachment of the first portion to the drug delivery device.

The cannula may have a reduced number of stress concentration points on the second portion of the tube. A focused stress concentration point may be formed on the cannula in the second portion.

In aspects, a cannula tip is angled. In some aspects, the tip may be angled at an angle of between about 10 and about 45 degrees. In further aspects, the cannula tip may include a first angled portion and a second angled portion, wherein the second angled portion is steeper than the first angled portion. In this configuration, the angles are generally in the same direction. The first angled portion may be angled at about 30 degrees, and the second angled portion may be angled at about 45 degrees. Alternatively, angles may be cut in opposite directions. As a further alternative, the tip could be cut with 3 or 4 or more angles. As another alternative, the tip may be angled in a curved manner.

In further aspects, the internal wall of the tube may be sized to fit a 30 gauge needle.

The tube may be comprised of a hyperelastic material, such as polyurethane. The tube may be comprised of polytetrafluoroethyle and/or fluorinated ethylene propylene.

The internal surface of the tube mall may include ribbing. The ribbing may be localized or run along the entire length of the cannula. The ribbing may be in parallel or perpendicular to the length of the cannula. The ribbing may be linear or helical/spiral, for example.

In aspects, a cannula is provided for use in a drug delivery system, the cannula comprising a tube adapted to be inserted subcutaneously through the skin of a patient, the tube having a wall with an internal surface and an external surface and having a first portion connected to a drug delivery device and a second portion, wherein the lower half of the tube is curved and includes a tip at the end of the tube opposite to the attachment of the first portion to the drug delivery device. The tube may be adapted to straighten when an insertion needle is used to insert the tube into the skin of a patient and adapted to return to being curved when the insertion needle is removed.

In aspects, the wall of the cannula is thicker at the tip than where the first portion transitions to the second portion of the cannula. The tube may include a slit through the wall in the second portion. The slit may be straight or helical, for example.

The various aspects discussed above may be used alone or in different combinations with each other.

BRIEF DESCRIPTION OF THE DRAWINGS

For a more complete understanding of the present disclosure, reference is now made to the following figures, wherein like reference numbers refer to similar items throughout the figures.

DETAILED DESCRIPTION

The following description and the drawings illustrate specific embodiments sufficiently to enable those skilled in the art to practice the system and method described. Other embodiments may incorporate structural, logical, process and other changes. Examples merely typify possible variations. Individual elements and functions are generally optional unless explicitly required, and the sequence of operations may vary. Portions and features of some embodiments may be included in, or substituted for, those of others.

The present description relates, generally, to delivery devices, systems and methods for delivering an infusion medium, such as a drug, to a recipient, such as a medical patient-user. Specifically, disclosed herein are infusion cannulas for improving the infusion of an infusion medium. While embodiments are described herein with reference to an insulin delivery example for treating diabetes, other embodiments may be employed for delivering other infusion media to a patient-user for other purposes. For example, further embodiments may be employed for delivering other types of drugs to treat diseases or medical conditions other than diabetes, including, but not limited to, drugs for treating pain or certain types of cancers, pulmonary disorders, or HIV. Further embodiments may be employed for delivering media other than drugs, including, but not limited to, nutritional media including nutritional supplements, dyes or other tracing media, saline or other hydration media, or the like. Also, while embodiments are described herein for delivering or infusion of an infusion medium to a patient-user, other embodiments may be configured to draw a medium from a patient-user. The designs disclosed herein according to one or more embodiments are low risk and realizable within a relatively short timeline, with a significant improvement in bend resistance.

The infusion cannula disclosed herein according to one or more embodiments is provided to deliver an infusion medium, such as a drug, to a patient, and can be used in conjunction with an infusion set, for delivery of that substance into a patient, such as into a patient's internal tissue environment. The infusion cannula comprises a tube having an inner lumen, defined by a wall with an internal surface and an external surface. In various embodiments, the tube comprises a material that is flexible and biologically compatible. Example materials that are suitable for forming cannulas include polytetrafluoroethylene (PTFE) and fluorinated ethylene propylene (FEP). The material may be an elastomeric material. Examples of elastomeric materials include, but are not limited to, polyurethane (e.g., Pellethane™, Dow Chemical Company, Midland, Mich., polytree, polyether(amide), PEBA (PEBAX™, Elf Atochem North America, Inc., Philadelphia, Pa.), thermoplastic elastomeric olefin (TEO), copolyesters (COPs), styrenic thermoplastic elastomer (e.g., Kraton™, GLS Corporation, McHenry, Ill.), ethylene vinyl acetate (EVA), silicone, or polyvinyl chloride (PVC). In various embodiments, the elastomeric material is selected to be sufficiently flexible and reduce kinking to accommodate subcutaneous placement without being so rigid as to damage subcutaneous tissues and organs or to cause great discomfort to a user. When considering which material to use, it should be considered whether the material can be used in a way that does not 100% block flow through the cannula in the event of a kink. Biologically compatible elastomeric materials minimize irritation and inflammation of biological tissues. In addition, compatibility between the elastomeric material and the substance to be delivered through the cannula should be taken into account. For example, polyolefin has been found to be more suitable for insulin delivery than PVC. The tube may include a coating adhered to the external surface of the tube, such as a biocompatible coating. Another potential coating could be a medicinal agent in a polymer matrix, for example as disclosed in U.S. Pat. No. 6,475,196, which is herein incorporated by reference.

In some configurations, the tube can comprise an inner layer of one material adhered to an outer layer of another material. One example would be an inner layer of polyolefin adhered to an outer layer of PVC, which can be adhered to one another by an interlayer of adhesive, such as ethylene-vinyl acetate. This particular multi-layer tube would combine the reduced binding, clogging, leaching and carbon dioxide penetration of polyolefin with reduced kinking and strength of PVC. Alternatively, the multiple materials may be co-extruded so adhesives are not required. In alternative configurations, the elastomeric material is selected so as to achieve the desired properties with a single, uniform material to avoid having to adhere one material to another. In further alternatives, it is not necessary to use only elastomeric materials. For example, a single strand of wire could be embedded in the cannula to provide rigidity or spiral bound wire could be embedded in the cannula.

In further embodiments, the cannula is made out of a hyperelastic material to prevent the cannula from becoming kinked as opposed to a material like PTFE which plastically deforms. Although a cannula made from a hyperelastic material could become momentarily kinked, after load removal it would revert to its pre-kinked state. For example, a polyurethane material may be used. When the polyurethane material is bent, in tests it generally collapsed by a greater margin than a PTFE type cannula. This indicates that while a polyurethane cannula may be resistant to permanent kinking that it may be more prone to temporary occlusions that occur when a load is applied to the cannula. However, the occlusions will resolve when the load is removed. The risk of occlusions can be further mitigated with further geometry changes and/or one or more other designs discussed herein, including choice of cannula material. Additional possible material options that behave like a hyperelastic material in this scenario include polyether block amides, silicones, or ethylene vinyl acetate. Alternatively, the cannula may be composed of a stiffer material closer to the delivery device and a more flexible material closer to the tip of the cannula. This could be accomplished either as a bonded assembly of multiple materials (during cannula fabrication or a secondary process) or by selectively adding material to the tip such as a plating or other coating. The cannula would then tend to gradually bend at the base rather than kinking at the tip.

A PTFE cannula was compared to a polyurethane material cannula. With the polyurethane material model, because the material was hyperelastic, no plastic deformation occurred and the cannula reverted to an unbent state after loading was removed. The inside diameter of the polyurethane material model collapsed by a greater margin than the PTFE cannula. This indicates that while a polyurethane cannula may be resistant to permanent kinking, it may be more prone to temporary occlusions that occur when a load is applied. However, these temporary occlusions resolve upon removal of the load. Moreover, with respect to actual use of a PTFE or polyurethane cannula, the user will have the cannula in his body for an extended period of time. With a PTFE cannula, if it becomes kinked, it will remain kinked, creating immediate risk of occlusions and increase further risks during use. With the hyperelastic material, the cannula would return to its original shape, resolving any occlusion and thereby decreasing long-term risk. This risk of occlusion could be mitigated by further geometry changes such as wall thickening or internal ribbing or non-circular cross-sections.

Typical cannulas for subcutaneous placement and delivery have a gauge sufficiently large to permit passage of the desired substance through the lumen and sufficiently small to minimize trauma to surrounding tissues, for example, the gauge can be between about 24 and about 30. Reducing the introducer needle outer diameter would enable a larger wall thickness to diameter ratio for the cannula. This would decrease the likelihood of kinking or inside diameter collapse when an axial compressive load is applied to the cannula. For example, cannulas with inner diameter sized for 29 gauge and 30 gauge could be used as opposed to a typical 27 gauge design. A typical cannula is about 6 mm or 9 mm in length. Other diameters, thicknesses and cannula lengths can be employed, so long as they are capable of delivering the desired substance into the appropriate location or tissue.

Even with use of flexible elastomeric materials in cannulas, they can kink, resulting in occlusion that can slow or stop delivery of the desired material to the user. Several designs are disclosed herein according to one or more embodiments that greatly reduce cannula occlusions.

Figure 1:
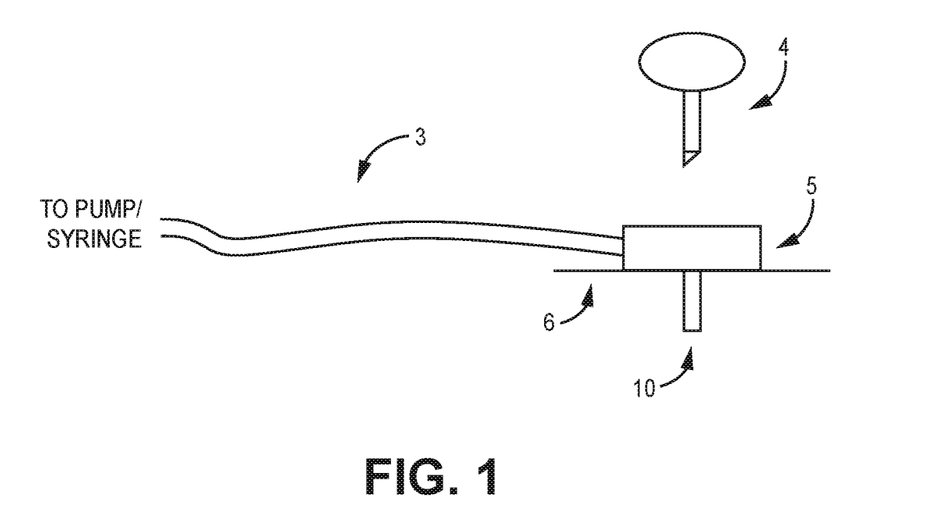
FIG. 1 illustrates a diagram of a drug delivery device, cannula, and insertion tool according to an embodiment.

FIG. 1 is a schematic illustration of an exemplary infusion set, which can incorporate a cannula 10 according to one or more embodiments of the present disclosure. The cannula 10 is attached to a cannula housing 5, which housing 5 is affixed to the skin of a subject, such as via an adhesive strip 6. Tubing 3 may extend from the cannula housing to a pump or syringe that delivers the desired substance to the cannula 10 via the tubing 3. An insertion needle 4 may be used to insert the cannula 10 through the subject's skin and into the underlying tissue. Some other infusion sets that may be used with the embodiments of the presently disclosed cannula, including those infusion sets that are combined with sensors, are disclosed in, for example, U.S. Pat. Nos. 5,851,197; and 6,293,925, which are herein incorporated by reference.

Figure 2:
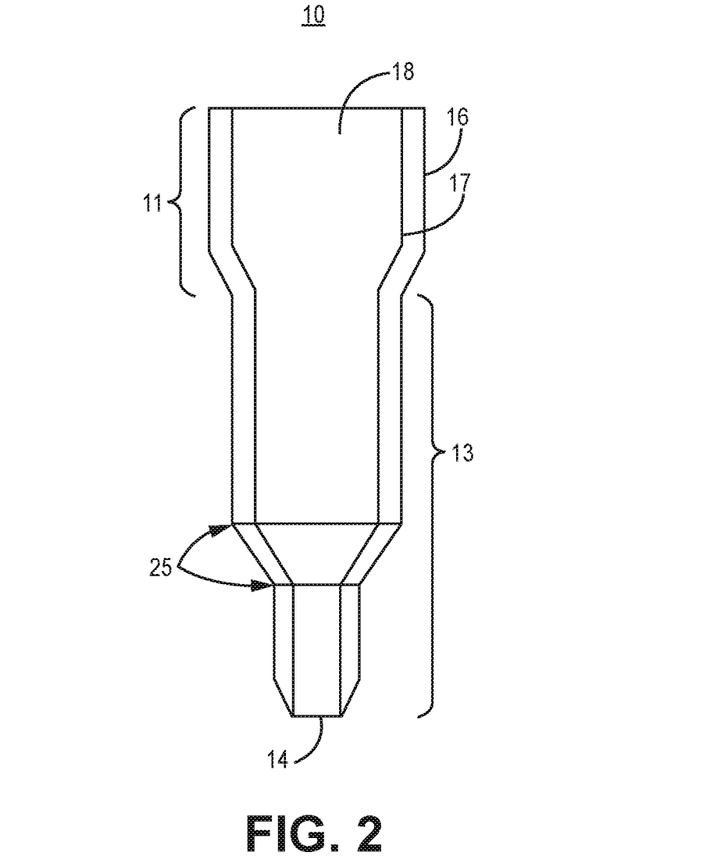
FIG. 2 illustrates a side view of a cannula.

FIG. 2 shows a basic cannula structure with a profile previously known in the art. Cannula 10 includes a first portion 11, which is adapted to be connected to a delivery device, and a second portion 13, which is adapted to be inserted into the skin of a patient. As shown in FIG. 2, the first portion 11 is wider than second portion 13, with a tapered bottom that leads to the second portion 13. In this particular prior art construction, the second portion 13 also tapers towards a tip 14, which is open and allows for flow of a substance such as insulin into the body of a patient. The cannula contains a wall with an external surface 16 and an internal surface 17. The internal surface forms a cavity 18 along the length of the cannula to allow for flow of the substance through the cannula. In the cannula shown in FIG. 2, the wall is composed of one material in one layer, but there could be additional layers of the same or different material if desired. In addition, the cannula can have more unusual materials, such as metallic strands running linearly to the cannula or in a spiral fashion. The wall at the second portion 13 tapers slightly from where the second portion 13 meets the first portion 11 until the tip 14. In addition, the wall tapers such that it is thinnest at the tip 14. The shape of the wall creates stress concentrations 25. As shown in FIG. 2, the stress concentrations tend to be at points in the cannula where the wall changes its angle. When a load, created by movement in the body, for example, is applied to the cannula, it can deform at these stress concentrations. This prior art cannula tends to bend at the stress concentrations 25 and, with currently used materials, permanently deform, creating occlusions that prevent or slow delivery of the desired substance to a user.

According to one or more embodiments, changing the shape of the cannula provides reduced risk of occlusion. By changing the geometry of the transitions, for example making the transition more gradual, it is possible to reduce the likelihood of kinking, which can be associated with occlusions. Diameter can be adjusted or materials can be altered to additionally reduce likelihood of kinking or as otherwise necessary. It is also possible to limit the number of transitions in a cannula, which will limit the stress concentrations, thereby limiting the locations at which kinking is likely to occur. It is noted that any changes to the geometry of the cannula should be balanced by any functional requirements relating to the fit of the cannula and the insertion needle, such as insertion reliability and introducer needle removal reliability. The higher the stress concentration is located, assuming a kink happens at that stress concentration, the less the angle of bending tends to be for a particular displacement of the cannula, thereby reducing the kinking risk.

Figure 3:
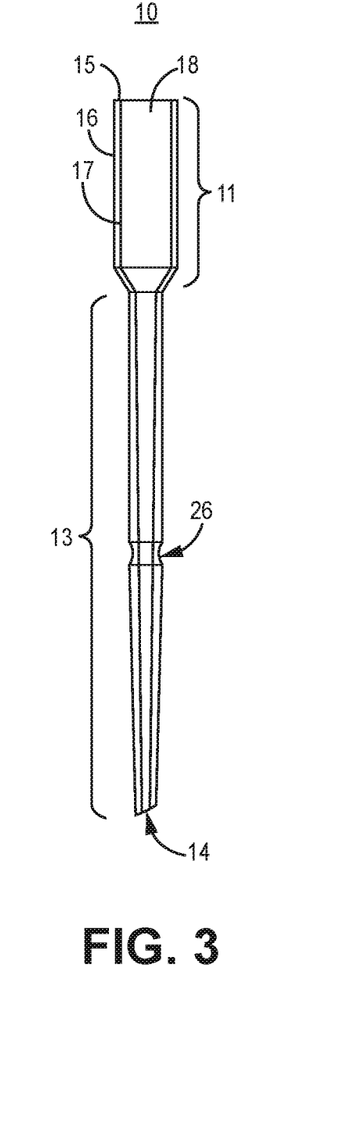
FIG. 3 illustrates a side view of a cannula according to an embodiment.

In one configuration, shown in FIG. 3 according to an embodiment, a stress concentration point 26 has been intentionally formed in the cannula 10 at approximately where the skin will interface with the subcutaneous tissue of the user. Thus, there will be more gradual bending of the lower portion 13 between the stress concentration point 26 and the tip 14 under axial compression. Deformation of the cannula, such as plastic deformation, for example, is reduced, and any kinks are more likely to recover. The stress concentration point is a predictable yield point, allowing for consistent performance of this design according to one or more embodiments. This design further reduces collapsing of the interior space of the cannula, which reduces occlusion risk. It is also envisioned that this design will reduce long term strain on tissue because the lower portion 13 in the subcutaneous tissue will be moving less. In various embodiments, the placement of the stress concentration works with a wide range of skin thicknesses.

To further reduce bending and kinking of the lower portion 13 between the stress concentration point 26 and the tip 14, ribbing may be included on the inner surface of the wall 15. Examples of ribbing are discussed herein. Although ribbing at least below the stress concentration point 26 is contemplated, it is possible to add ribbing to the entire cannula 10 or to the entire lower portion 13, including or excluding the stress concentration point 26. In various embodiments, the stress concentration point 26 can be excluded from any ribbing to allow movement at that point and to divert movement from the rest of the cannula 10. It is also possible to locally thicken the wall 15 between the stress concentration point 26 and the tip 14. Currently, the wall 15 narrows as it reaches the tip 14, but keeping it as thick as the remainder of the wall, or thickening it further at the tip, can reduce bending. Another addition to the stress concentration design would be to use local heat treatment to change the properties of the cannula 10 in particular areas. For example, flexibility could be added in the stress concentration area 26 and/or increased stiffness could be added above and/or below the stress concentration area 26 to reduce bending in that area and focus the stress at the stress concentration point.

By choosing an appropriate ratio of cannula wall thickness to diameter of the cannula, the magnitude of the inside diameter collapse and the likelihood of kinking could be reduced or eliminated. This could either be done using prior art cannula materials such as PTFE or a hyperelastic or otherwise more ductile material or incorporating multiple materials, making the cannula a composite design. Wall thickness changes can pose some risks, because the cannula inside diameter and/or its outside diameter would have to change to accommodate a wall of a different thickness. A larger cannula could impact insertion and comfort, and a smaller inside diameter, and consequently a smaller insertion needle, could impact insertion as well.

One variant of a wall thickness change would be to have an interference fit between inside diameter of the cannula and the introducer needle. This would allow a current introducer needle size to be used while reducing the impact of the increase in cannula diameter. A hyperelastic or otherwise more ductile and creep resistant material may be used for the interference fit. Benefits from this design would occur both pre and post insertion. The pre-load and friction between the cannula and introducer needle would effectively increase the column strength of a hyperelastic cannula during insertion, possibly increasing insertion reliability relative to an identical cannula on a smaller needle without interference. Further, the effect of Poisson's ratio means that the wall thickness during insertion when the cannula is stressed will be slightly less than the wall thickness post insertion. As strain from the interference fit with the introducer needle stretches the cannula, the wall thickness of the cannula will be reduced. When the introducer needle is removed, and the interference is resolved, the wall thickness will increase again. This may benefit comfort during insertion relative to a larger cannula with identical wall thickness and increased inner diameter to accommodate the same introducer needle without interference. The pre-stressed cannula will be smaller during insertion. With the interference fit, as the cannula shrinks after needle removal, it may also be more comfortable during normal wear.

In further embodiments, a tapered introducer needle may be used. If a thick walled, creep resistant hyperelastic cannula is installed on a tapered needle with an interference fit, its column strength will be effectively increased during insertion. This is because it would require more force to push a cannula up a tapered needle than up a straight needle, assuming there is interference or line to line contact between the cannula and needle. The tapered needle should also aid in introducer needle removal for an interference fit as the friction would drop as the needle is withdrawn and the interference drops. The cannula itself does not have to be tapered, although it may be. The cannula tip may be angled, as discussed herein, or straight.

Other variants are possible to reduce stress or to focus stress at desired points of the cannula. These variants may be made in addition to or as an alternative to the stress concentration design of the embodiment of FIG. 3. For example, an angled tip may be included, which is discussed further herein. The angled tip makes it more likely to induce gradual lateral bending than buckling. The angled tip may have a variable angle to make it less likely to dig into the tissue. Different materials may be used, as discussed above, such as a more flexible and/or tougher material than the currently used materials like PTFE. A more flexible material, such as the elastomer examples discussed herein, would reduce the likelihood of permanent kinking and occlusion while a tougher material would reduce the likelihood of kinking at all. It is noted that when choosing what material to use, the patient's comfort should always be considered. A too tough material, such as a stainless steel needle in lieu of a polymer cannula, could result in discomfort from lack of movement with the body.

In addition to the stress concentration designs and other designs discussed above, the cannula may be given a degree of freedom so that it may move at its connection to the delivery device, for example at a cannula housing that is adapted to sit on the skin of a patient. An elastomer or rotational/pivot joint could be included at the cannula housing. For example, the cannula housing may include a flexible member holding the cannula and allowing for axial and rotational degrees of freedom. Alternatively, a joint such as a ball joint could be included, also allowing for axial and rotational degrees of freedom. After an initial slight misalignment or buckling, any force would be focused into the connection with the cannula housing, allowing motion at that connection rather than buckling or kinking of the cannula itself.

Figure 4:
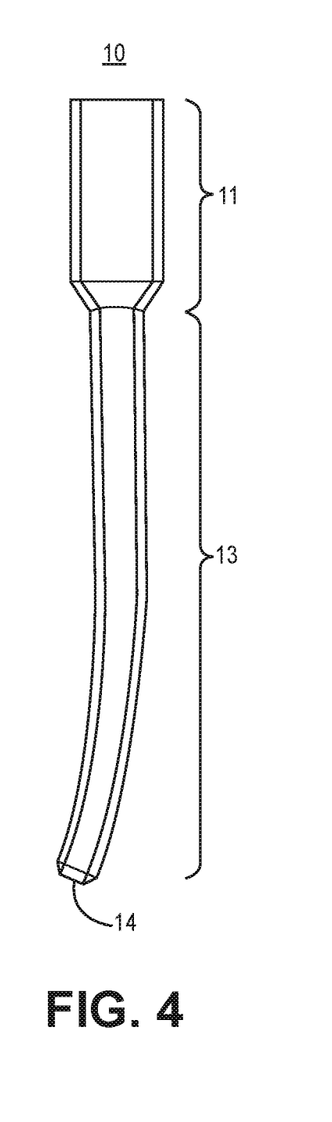
FIG. 4 illustrates a side view of a cannula according to an embodiment.

In further embodiments, as shown in FIG. 4, the cannula 10 may be curved in the lower portion 13. When the cannula 10 is inserted into the body of a patient using a needle, it will be straight, because the straight needle is holding it in a straight position. Once the needle is removed, the cannula 10 reverts to a curved shape, as shown in the embodiment of FIG. 4. The curved shape biases the cannula to bend during axial compression rather than buckling or kinking. Because of the curved shape, stress is distributed evenly, reducing plastic deformation for a given axial displacement and giving a better chance for any kinks to recover. The curved shape also reduces inner collapse of the cannula, which can reduce occlusion risk. With the evenly distributed stress, it is envisioned that there may be less stress on tissue from reduced kinking and bending at individual stress points.

In addition to using a curved cannula, the other variants discussed herein may be used. For example, the tip 14 may be angled. The material used to form the cannula may be more flexible and/or tougher than currently used materials. There may be a degree of freedom, for example from an elastomer connection or ball joint, at the cannula housing. Locally thickened walls at the tip could be used, and local ribs, or ribs throughout the cannula, could be used to increase thickness and strength. Any combination of these improvements could be used to produce a cannula that reduces kinking.

Figure 5:
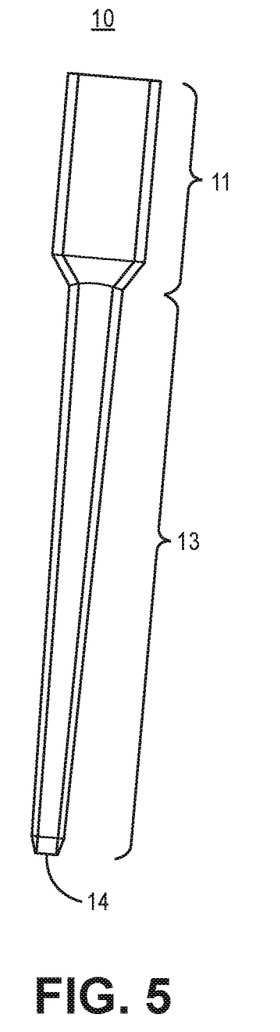
FIG. 5 illustrates a side view of a cannula according to an embodiment.

In another embodiment, as shown in FIG. 5 a slight angle relative to insertion may be imparted into a cannula after insertion. This slight angle biases the cannula to bend gradually rather than buckling. This change could be made entirely by adjusting an insertion tool or cannula housing without having to make any changes to the cannula itself. An angle of between about 10 and 30 degrees would be sufficient to induce bending rather than buckling. The angle reduces plastic deformation for a given axial displacement and makes it more likely for kinks to recover. The angled cannula is further less likely to have internal collapse, which may reduce occlusion risk. It is further envisioned that the angled cannula will put less long term strain on tissue by reducing localized movement.

The same variants discussed with respect to the curved cannula design of FIG. 4 may be used in conjunction with the angled cannula design of FIG. 5.

Figure 6:
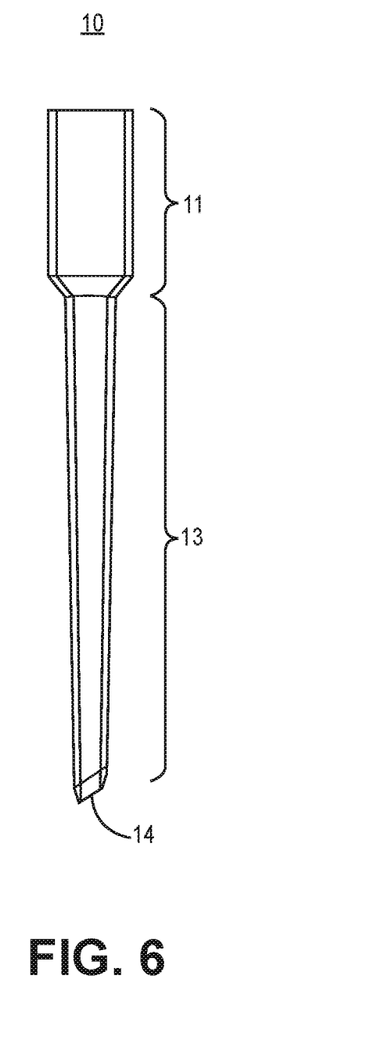
FIG. 6 illustrates a side view of a cannula according to an embodiment.

As an alternative, or in addition to other designs disclosed herein, an angled tip may be used, as shown in the embodiment of FIG. 6. The cannula 10 includes a tip 14 that is angled. An angled tip, for example, of between about 10 degrees and about 45 degrees is more likely to induce gradual lateral bending than buckling like a straight tip. There are several configurations of an angled tip that can be used. A first configuration would be a simple single angled cut, as shown in the embodiment of FIG. 6. In various embodiments, the angled tip can be between about 10 degrees and about 45 degrees. In some embodiments, the angled tip can be between 30 and 45 degrees. It should be noted that according to one or more embodiments, the angled tip may be of a certain angle dependent on a length of the cannula, materials, etc.

Figure 10:
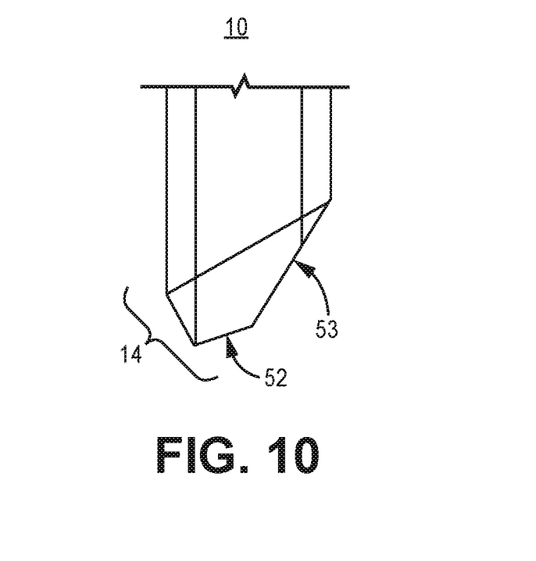
FIG. 10 illustrates a partial, side view of a cannula according to an embodiment.
Figure 11:
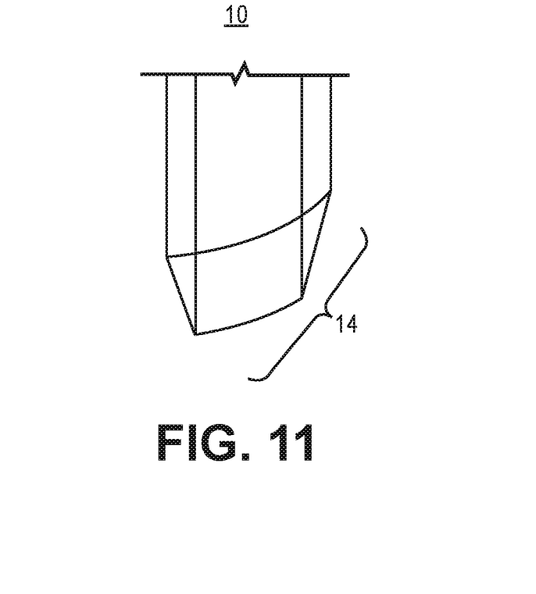
FIG. 11 illustrates a partial, side view of a cannula according to an embodiment.

In an implementation according to another embodiment, the tip has a minimum of two angled cuts. As shown in the embodiment of FIG. 10, the tip 14 has 2 cuts. The first cut 52 is a gradual angle on one side, and the second cut 53 is a steeper angle on the other side. The use of the two cuts prevents a knife edge that would cause the tip of the cannula to dig into tissue. In one or more embodiments, the gradual angle is less than about 30 degrees and the steeper angle is more than about 45 degrees. In various embodiments, the first cut 52 can be an angle between 10 and 30 degrees, and the second cut 53 can be an angle of between 45 and 65 degrees. In an embodiment, the first cut 52 is a gradual angle of 15 degrees, and the second cut 53 is a steeper angle of about 57 degrees, for example 57.5 degrees. In an embodiment, the first cut can be an angle between 10 and 20 degrees, and the second cut 53 can be an angle between 35 and 65 degrees. In another embodiment, the first cut can be an angle between 10 and 20 degrees, and the second cut 53 can be an angle between 35 and 55 degrees. In other various embodiments, the first cut 52 can be an angle in any of the ranges including: 0 to 30 degrees, 5 to 30 degrees, 10 to 20 degrees, 10 to 30 degrees, 5 to 25 degrees, 5 to 20 degrees, 15 to 30 degrees, 15 to 25 degrees, 15 to 20 degrees, or the like, and the second cut 53 can be an angle in any of the ranges including: 35 to 65 degrees, 45 to 55 degrees, 45 to 70 degrees, 30 to 70 degrees, 30 to 65 degrees, 30 to 60 degrees, 30 to 55 degrees, 35 to 70 degrees, 35 to 60 degrees, 35 to 50 degrees, 35 to 45 degrees, 40 to 70 degrees, 40 to 65 degrees, 40 to 60 degrees, 40 to 55 degrees, 40 to 50 degrees, 40 to 45 degrees, 45 to 65 degrees, 45 to 60 degrees, 45 to 50 degrees, or the like. Any number of cuts greater than two may be made between the gradual and steep angles. In various embodiments, steeper tip angles, for example where the second cut 53 has an angle of about 70 degrees, may be used; however, the length of the cannula would increase accordingly to accommodate the steeper angle and resulting cut. As the number of cuts approaches infinity, the cut effectively becomes a smooth radius shape between the gradual and steep angles, as shown in the embodiment of FIG. 11. A further refinement would be to have multiple angles on the tip in multiple directions/planes of cutting/forming. Particular embodiments may have 3, 4, or 5 cuts with angles spread appropriately and may be of any of the ranges above. This could induce bending in multiple directions as opposed to just one.

The use of an angled tip has several benefits. For example, it induces gradual bending of the cannula rather than buckling. Comparisons between angled tips and non-angled tips show that the angled tip bends much more gradually and does not collapse inward like the straight tipped baseline cannula. Moreover, the angled tip compresses less than the straight tip, reducing compression and bending of the entire cannula.

Figure 7A:
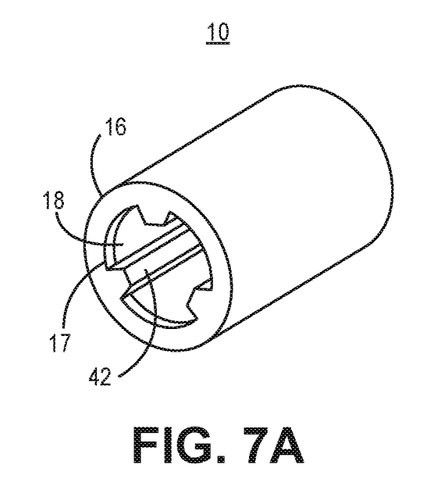
FIG. 7A illustrates a perspective, partial view of a cannula according to an embodiment.
Figure 7B:
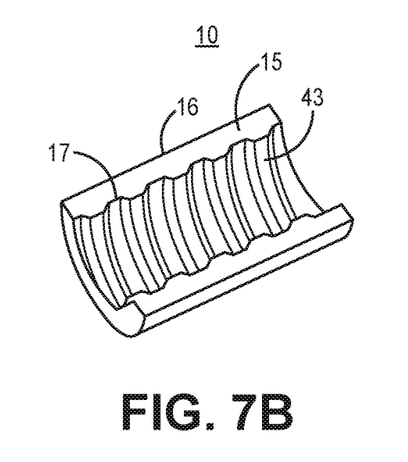
FIG. 7B illustrates a perspective, partial view of a cannula according to an embodiment.

In further embodiments, for example as shown in FIGS. 7A-7B, ribbing can be used to strengthen the internal surface 17 of the cannula wall 15. The ribs can be added in localized areas of the cannula or along the entire length of the cannula. FIG. 7A shows a partial view of a cannula 10 including a straight rib pattern according to an embodiment, where the ribs 42 run parallel to the length of the cannula 10. FIG. 7B shows a rib pattern according to another embodiment, where the ribs 43 run perpendicular to the length of the cannula 10. The ribbing may be part of a composite design, or may be used along with other novel features discussed herein. For example, the rib 42 or spiral ribs 43 may be made out of a rigid thermoplastic or metallic material running the length of the rib/spiral.

The ribs may be formed via any suitable approach, such as a cold forming process. Ribbing provides resistance to kinking, while overall having a more flexible and comfortable cannula and a greater flow area through the cannula. Ribbing such as a helical or straight ribbed version, where the rib is predominantly triangular in cross section may provide an additional benefit over uniform thickening. Ribbing can allow for a tighter fit along a longer length of the introducer needle without increasing friction between the cannula and the needle by as much as if the entire wall were in contact with the needle. Low friction is beneficial as it reduces the forces needed for insertion needle removal.

The crests of triangular ribs in contact with an introducer needle have high local stresses at their contact points that can take a compression set more quickly. This will reduce contact pressure and therefore friction between the cannula and the introducer needle by a greater amount than a more uniformly contacting thick wall would have. If the ribs are designed with an aspect ratio such that their height is larger than the width of their base, they can also bend around the introducer needle rather than compressing directly. This will apply less friction to the introducer needle than a uniformly thick wall. Offsetting the ribs such that the crest of the triangle is not directly in line with the central axis will make it more likely to bend the ribs and receive the low friction benefit.

Linear ribs that run along the length of the cannula, parallel to the length, are easy to manufacture. Helical versions are more difficult to manufacture but come with increased kink resistance, and potentially greater flexibility in bending for a given level of kink resistance, resulting in improved comfort. Another ribbing variant would be either a helical or repeating annular ring of ribs whose triangular peaks were oriented in a manner such that they facilitate needle removal but resist movement of the cannula along the needle during insertion. This reduces the likelihood of cannula accordioning or buckling during insertion while maintaining ease of introducer needle removal.

It is also possible to use locally thickened walls, such as at the tip of the cannula, as discussed above, on their own and without any other cannula modifications.

Figure 8:
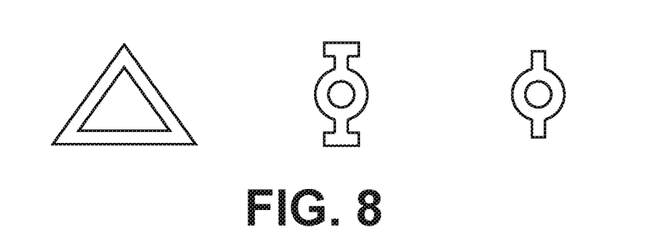
FIG. 8 illustrates cross-sectional views of several cannulas according to one or more embodiments.

In further embodiments, the cannula may have cross-sections that are not strictly circular. For example, some potential alternate cross-sections are shown in FIG. 8. Potential shapes could include triangular cross-sections or cross-sections that are based in circular shapes but with extensions in various directions. Shapes such as those shown in FIG. 8 may add strength or stiffness. The alternate cross-sections may be localized or throughout the length of the cannula.

Figure 9A:
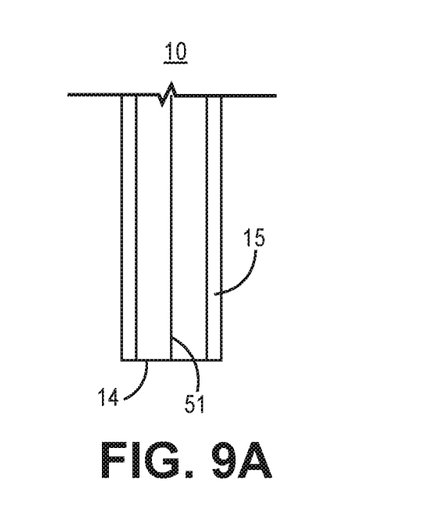
FIG. 9A illustrates a partial, side cut-away view of a cannula according to an embodiment.
Figure 9B:
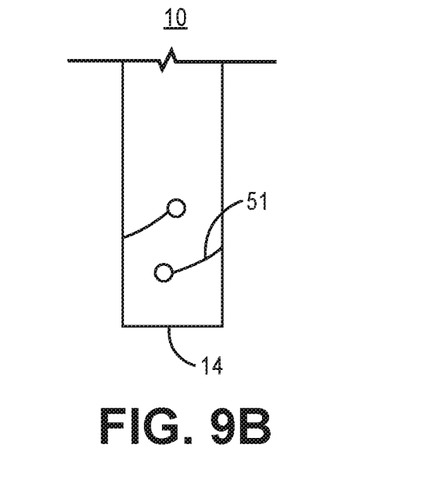
FIG. 9B illustrates a partial, side cut-away view of a cannula according to an embodiment.

Another potential approach to reducing kinks is shown in the embodiments of FIGS. 9A and 9B. A slit 51 may be introduced into the side of the cannula wall 15. During any compression of the cannula 10, the slits will open up to allow flow out of the slits. The slits may be used in addition to any of the other designs shown herein. The slits are generally partially in the cannula. For example, they may be constrained to no closer than 4 mm to the top of the cannula. If the slit is too high up the cannula, the risk of leaks increases. The embodiment of FIG. 9B illustrates cutouts, for example in the shape of a circle, that may be included at an end of a slit 51, which are stress relief cutouts to prevent the slits from propagating into cracks.

It is possible to use the above design variants in various combinations with one or more of the designs to improve stability of the cannula. For example, some variations that show greater resistance to kinking are an angled tip with 30 or 29 gauge opening in the cannula, and PTFE or FEP as the cannula material.

In further embodiments, a smart insertion device may be used to insert the cannula. The insertion device evaluates tissue at a particular insertion location and informs the user if the site is appropriate for the cannula that it is inserting. The evaluation may determine whether the site is a location likely to bring increased kinks or other deformations of a cannula. The benefit of using a smart insertion device is that it is possible to reduce the interaction between cannula and muscle tissue, which can lead to kinking. The sensing of the tissue area may be purely mechanical, for example essentially a durometer evaluation of the site. Another method of sensing may be electromechanical, such as ultrasound, allowing for more robust evaluation methods. In lieu of just alerting or informing the user of a location being a bad insertion site, the smart insertion device may physically prevent insertion of the cannula.

It is possible to use an algorithm to determine whether a user is at particular risk for a bent cannula. Those users may then choose infusion sets with cannulas that have a lesser probability of kinking given the insertion location/composition.

While the description above refers to particular embodiments of the present disclosure, it will be understood that many modifications may be made without departing from the spirit thereof. The accompanying claims are intended to cover such modifications as would fall within the true scope and spirit of the present disclosure.

The presently disclosed embodiments are therefore to be considered in all respects as illustrative and not restrictive, the scope of the disclosure being indicated by the appended claims, rather than the foregoing description, and all changes which come within the meaning and range of equivalency of the claims are therefore intended to be embraced therein.

What is claimed is:

1. A cannula for use in a drug delivery system, the cannula comprising:
   a tube adapted to be inserted into skin of a patient, the tube having a wall with an internal surface and an external surface and having a first portion adapted to be connected to a drug delivery device and a second portion extending in an opposite direction than the drug delivery device relative to the first portion, wherein the second portion includes a tip at an end of the tube opposite to the first portion, the tip having a proximal end and a distal end, and wherein the distal end of the tip includes a first angled portion and a second angled portion, wherein the second angled portion is steeper than the first angled portion;
   the second portion including a stress concentration point formed therein as a yield point for bending of the tube; and
   the internal surface of the wall including ribbing only in a localized area between the stress concentration point and the tip to reduce bending and kinking of the second portion between the stress concentration point and the tip.

2. The cannula of claim 1, wherein the wall of the tube forms a cavity inside the cannula sufficiently big to fit about a 30-gauge needle.

3. The cannula of claim 1, wherein the first angled portion is at an angle of about 30 degrees and the second angled portion is at an angle of about 45 degrees.

4. The cannula of claim 1, wherein the first angled portion and the second angled portion of the tip are curved.

5. The cannula of claim 1, wherein the tube is comprised of a hyperelastic material.

6. The cannula of claim 5, wherein the hyperelastic material is polyurethane.

7. The cannula of claim 1, wherein the tube is comprised of fluorinated ethylene propylene.

8. The cannula of claim 1, wherein the ribbing runs in parallel with a length of the cannula.

9. The cannula of claim 1, wherein the ribbing runs perpendicular to a length of the cannula.

10. The cannula of claim 1, wherein the wall is thicker at the tip of the cannula than at the second portion where the second portion meets the first portion.

11. The cannula of claim 1, wherein the tube includes a slit through the wall in the second portion of the tube.

12. The cannula of claim 1, wherein the tube has a cross-section that is triangular.

13. A cannula for use in a drug delivery system, the cannula comprising:
   a tube adapted to be inserted into skin of a patient, the tube having a wall with an internal surface and an external surface and having a first portion adapted to be connected to a drug delivery device and a second portion extending in an opposite direction than the drug delivery device relative to the first portion, wherein the second portion includes a tip at an end of the tube opposite to the first portion, the tip having a proximal end and a distal end, wherein the distal end of the tip includes a first angled portion and a second angled portion, wherein the second angled portion is steeper than the first angled portion, and wherein the second portion of the tube is curved, and wherein the second portion of the tube is adapted to straighten when an insertion needle is used to insert the tube into the skin of a patient and adapted to return to being curved when the insertion needle is removed;

the second portion including a stress concentration point formed therein as a yield point for bending of the tube; and the internal surface of the wall including ribbing only in a localized area between the stress concentration point and the tip to reduce bending and kinking of the second portion between the stress concentration point and the tip.

* * * * *